(12) United States Patent
Denoual

(10) Patent No.: US 9,121,006 B2
(45) Date of Patent: Sep. 1, 2015

(54) DEVICE FOR MONITORING CELL CULTURE DEVELOPMENT

(75) Inventor: Matthieu Denoual, Caen (FR)

(73) Assignee: CENTRE NATIONAL DE LA RECHERCHE SCIENTIFIQUE (CNRS), Paris (FR)

( * ) Notice: Subject to any disclaimer, the term of this patent is extended or adjusted under 35 U.S.C. 154(b) by 499 days.

(21) Appl. No.: 13/502,170

(22) PCT Filed: Oct. 4, 2010

(86) PCT No.: PCT/EP2010/064733
§ 371 (c)(1),
(2), (4) Date: Apr. 16, 2012

(87) PCT Pub. No.: WO2011/047954
PCT Pub. Date: Apr. 28, 2011

(65) Prior Publication Data
US 2012/0200305 A1  Aug. 9, 2012

(30) Foreign Application Priority Data
Oct. 19, 2009  (FR) ...................................... 09 57307

(51) Int. Cl.
*C12M 3/00* (2006.01)
*C12M 1/00* (2006.01)
*C12M 1/34* (2006.01)

(52) U.S. Cl.
CPC ............... *C12M 41/46* (2013.01); *C12M 41/36* (2013.01)

(58) Field of Classification Search
CPC ...... C12M 41/46; C12M 41/48; C12M 41/22; C12M 41/16; C12M 41/18; C12M 41/12
See application file for complete search history.

(56) References Cited

U.S. PATENT DOCUMENTS

| | | | |
|---|---|---|---|
| 2005/0142537 A1* | 6/2005 | Rieder et al. | 435/5 |
| 2009/0075362 A1 | 3/2009 | Baumfalk et al. | |
| 2009/0081721 A1* | 3/2009 | Meyer et al. | 435/34 |
| 2009/0263856 A1* | 10/2009 | Bashir et al. | 435/29 |

FOREIGN PATENT DOCUMENTS

| | | |
|---|---|---|
| DE | 20 2007 005 399 U1 | 8/2007 |
| EP | 0 036 274 A2 | 9/1981 |

(Continued)

OTHER PUBLICATIONS

Tlili et al., "Fibroblast Cells: A Sensing Bioelement for Glucose Detection by Impedance Spectroscopy," Anal. Chem., vol. 75, pp. 3340-3344, 2003.

(Continued)

*Primary Examiner* — Nathan Bowers
(74) *Attorney, Agent, or Firm* — Foley & Lardner LLP

(57) ABSTRACT

According to the invention, an electrical heating resistor (1) is in contact with a receiving surface for heating a cell culture (CC), the resistor being connected to an electric circuit for providing heating power so as to keep the cell culture (CC) at a prescribed temperature setting (Tref). An element (61) for measuring at least one first parameter (VM), representing the amount of heating power used by the circuit, said measuring element (61) is also an element (61) for measuring the development of the cell culture, the device comprising a computer (62, 63) for calculating a second parameter (PAR), representing the development of the cell culture (CC) over time, on the basis of the first parameter (VM).

16 Claims, 6 Drawing Sheets

(56) References Cited

FOREIGN PATENT DOCUMENTS

Figure 3:
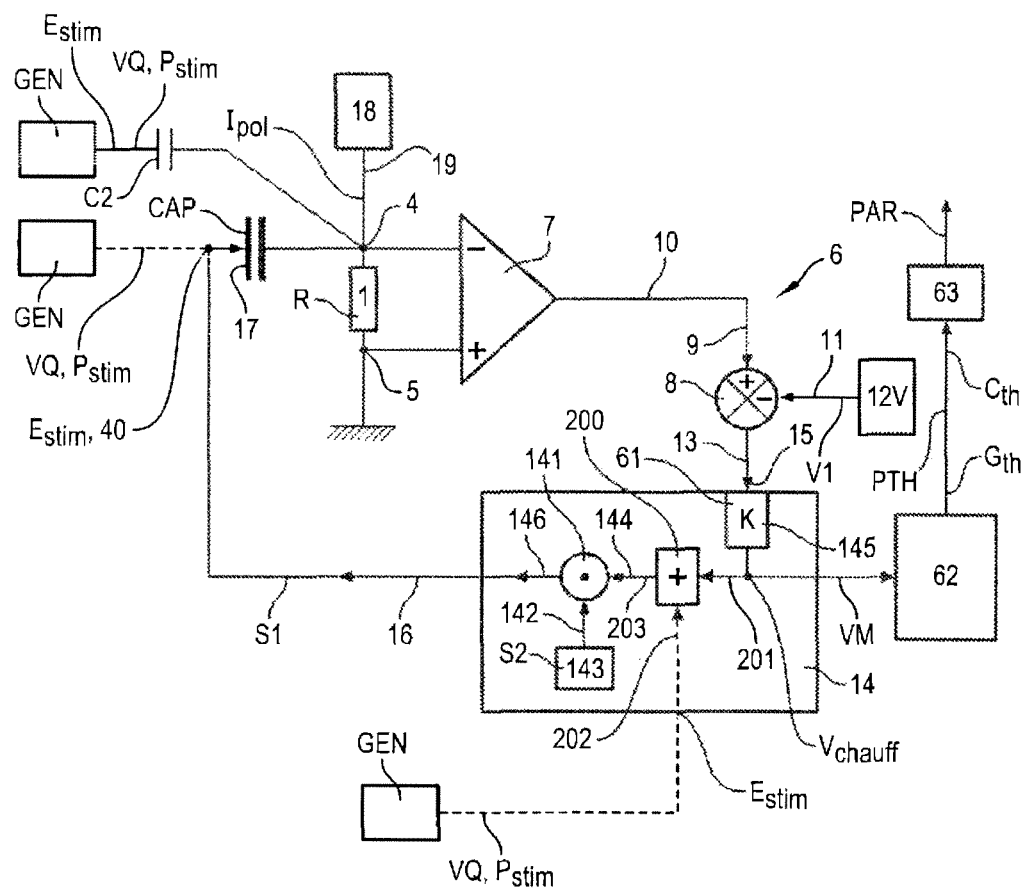

WO  WO 2006/071800 A1  7/2006
WO  WO 2009/034066     5/2009

OTHER PUBLICATIONS

International Search Report issued in application No. PCT/EP2010/064733 on Jun. 29, 2011.

Wang, H, et al., "Analysis of the 3-omega method for thermal conductivity measurement", International Journal of Heat and Mass Transfer, vol. 52 (2009), pp. 2102-2109.

Gheorghiu, E. et al., "Monitoring cell cycle by impedance spectroscopy: experimental and theoretical aspects" Bioelectrochemistry and Bioenergetics, vol. 45 (1998), pp. 139-143.

Tlili, C., et al., "Fibroblast Cells: A Sensing Bioelement for Glucose Detection by Impedance Spectroscopy", Anal. Chem., vol. 75, (2003), pp. 3340-3344.

Božičević, Juraj et al., "Determination of Thermal Conductivity in Liquids by Monitoring Transient Phenomenon", Proceedings, XVII IMEKO World Congress, Metrology in the $3^{rd}$ Millennium, Jun. 22-27, 2003, Dubrovnik, Croatia, pp. 1699-1701.

Choi, Sun Rock, et al., "Amicromachined AC thermal sensor for monitoring the liquid-gas interface in a microchannel", Sensors and Actuators A, vol. 150, (2009), pp. 40-45.

\* cited by examiner

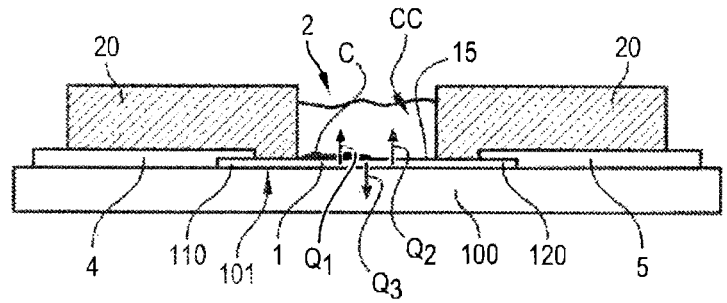
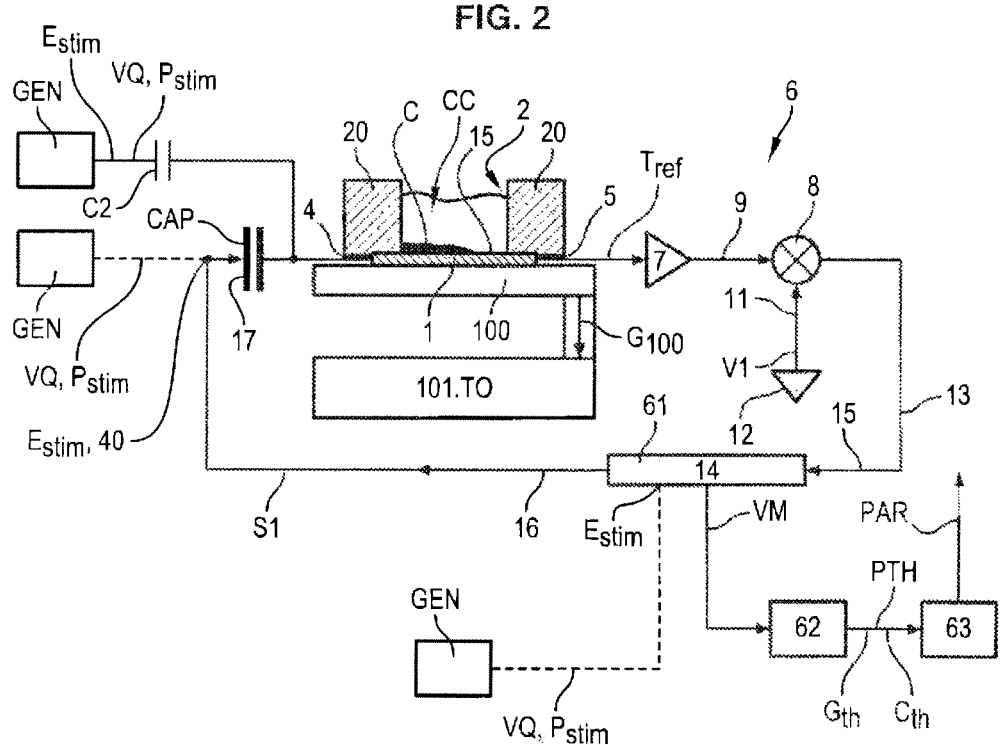

DEVICE FOR MONITORING CELL CULTURE DEVELOPMENT

The invention relates to a device for monitoring cell culture development.

The invention applies to the general field of biology.

The invention relates to the control (monitoring) of cell cultures, that is, the real-time tracking of the development of a cell culture.

Different scientific publications are known on the control of cell cultures.

Document [1] describes the control of cells by impedance spectroscopy.

Document [3] relates to the determination of thermal conductivity in liquids by means of a measuring probe.

Document [4] describes a thermal sensor for controlling the liquid-gas interface in a micro-channel.

Document [5] relates to a device for monitoring cell culture development, comprising a receiving surface of the cell culture, the receiving surface being in contact with electrical impedance arranged to have an impedance time value influenced by the presence of cells.

Conventional solutions for measuring thermal parameters known by document [4], and for example the 3-omega method according to document [2] are not applicable in the case of cell cultures due to harmful variations in temperature for the culture which they entail. In fact, the principle of these methods is to apply heat stimulation and then measure the corresponding variation in temperature.

The control of cell culture consists of quantitative and/or qualitative tracking of the development of cell cultures on lames or in culture wells. These cell cultures can be subject to external biochemical agents. The impact of these agents on the cultures can be revealed on the growth rate of cultures and/or on the morphology of cells. Conventionally, cell cultures subjected to an external agent are observed regularly over time by microscope and optionally compared to reference cultures not subjected to the agent. The evolution of the cell population over time and/or the evolution of the morphology of the cells are an indication of the effect of the external agent on the cells. This type of test for example distinguishes toxic agents from non-toxic agents on any cellular type.

Well plates are used to make several cultures so as to multiply conditions for testing, multi-agent, multi-concentration, cellular multi-type, multi-test conditions for statistics.

Legislation in force, REACH for example, aiming to test the toxicity of biochemical products and needs relevant to the development of molecules or biomedical techniques tend to considerably multiply the number of tests to be conducted. The miniaturisation of culture supports via an increase in the number of well per plates reduces the costs of tests and boosts rates. On the contrary, control techniques are still based on microscopy imaging and counting by image analysis.

Both non-integrated solutions and integrated solutions are known for controlling cell cultures.

Non-integrated solutions relate to external monitoring devices. In this case, the cultures are made on plates with or without wells then analysed by the external device. The most widely used solution is observation of the culture by microscopy with or without fluorescence. Other techniques in current research are based on external detection systems designed to be immersed in the cell culture solution to evaluate its development by way of impedance measuring, detection of biochemical particles, measurements of electric or magnetic fields.

Integrated solutions in current research are generally based on the integration of non-integrated solutions. These include optical devices with image acquisition integrated under the culture wells or electrical devices such as electrode systems for impedance analysis, detection of biochemical particles or measurements of electrical or magnetic fields.

With respect to the solution with optical system integrated under the culture wells, the principal drawback here is cost since it involves integrating optical sensors of CCD type for example under each of the wells in a one-off mechanism (disposable for sterility reasons). Also, from the production viewpoint, the integration of an optical sensor is not currently easy in mass mode due to compatibility problems between plastic processes (plastic injection), hot and subpressure processes, and restrictions as to tolerances of electronic systems. Also, focussing for cleanness of the image in this case is impossible and therefore this type of device requires considerable mastery for placing the sensor and the quality of the plastic moulding.

The most advanced integrated solution rests on the electrical principle of impedance analysis according to documents [1] and [5], that is, measurement of variation in impedance between electrodes to ascertain variation in cell population. The sensitivity of the system adapted to the detection of a single cell in micro-channels to date is limited in terms of application of monitoring seeking to evaluate the development of cell cultures. In addition, the integration of conductive electrodes, often opaque, into the wells limits the transparency of the support useful for the observation of cells by microscope for visual confirmation or fine observation of the morphology of cells. And, the use of current in the solution can cause phenomena disturbing the development of the culture linked to electrochemical oxidation and reduction phenomena occurring at the level of electrodes releasing particles. The very development of the cell culture releasing ionic components in the solution modifies the polarisation conditions and interferes with measuring. Solutions using three electrodes and special material in the form of a membrane are proposed to rectify this problem.

The use of measuring fields magnetic to track a cell culture requires magnetic micro/nanoparticles to hook onto cells so they are distinguished from the culture medium. The disadvantage of this hooking of particles, which can prove costly to execute, also disrupts natural growth conditions. Also, the measured signal, if particles are not added to the growth rhythm, will diminish at the rhythm of the cellular divisions.

The aim of the invention is to provide a device for monitoring cell culture development, which improves devices known from the prior art.

To this end, a first subject matter of the invention is a control device for monitoring the development of at least one cell culture, comprising a receiving surface for receiving of the cell culture, the receiving surface being in contact with electrical impedance arranged to have an impedance time value influenced by the presence of cells in the cell culture, characterised in that the impedance comprises at least one electrical heating resistor in contact with the receiving surface for the heating of the cell culture, the resistor being connected to an electrical circuit for supplying heating energy to the resistor, the resistor being variable as a function of the temperature and located in a heat control loop forming the electric heating circuit to maintain the cell culture at a prescribed setpoint temperature, the heat control loop comprising at least one measuring element for measuring at least one first parameter representative of the quantity of heat energy consumed by the electrical circuit, this measuring element serving also as measuring element for measuring the development of the cell culture, the measuring element being distinct from the resistor, the device further comprising at least one calculator for calculating from the first parameter representative of the quantity of heat energy consumed by the electrical circuit at least one second parameter representative of the time development of the cell culture.

In accordance with other characteristics of the invention,

The device comprises a generator of a predetermined external thermal stimulation signal connected to a determined point of the heat control loop, the calculator being provided for calculating from the first parameter representative of the quantity of heat energy consumed by the electrical circuit at least one third thermal parameter, the third thermal parameter being calculated by the calculator from the response of the resistor to the external thermal stimulation signal, said second parameter representative of the time development of the cell culture being calculated by the calculator from said third thermal parameter.

The thermal parameter comprises the thermal capacity of the resistor when it is in the presence of the cell culture and/or the thermal conductance of the resistor when it is in the presence of the cell culture.

The external thermal stimulation signal is applied to one of the terminals of the resistor by means of at least one electric capacitor.

The external thermal stimulation signal is applied to an adding module comprising a first input on which is the measured signal, a second input connected to the determined point of the heat control loop, to which the external stimulation signal is applied, and an output supplying a servo signal of the resistor equal to the sum of the signals present on the first input and on the second input.

The external thermal stimulation signal is in the form of an electric signal having a frequential component of zero mean.

Or the external thermal stimulation signal is in the form of an electric impulse signal.

The electrical heating resistor forms at least partly the receiving surface of the cell culture.

Or the receiving surface of the cell culture is provided on electrically insulating material interposed between the electrical heating resistor and the cell culture.

The electrically insulating material interposed between the electrical heating resistor and the cell culture is fixed removably relative to the electrical heating resistor.

The resistor is metallic with a thickness of between 5 and 20 nanometers.

The resistor comprises a first end connected to a first electrical contact and a second end connected to a second electrical contact, the resistor having between the first end and the second end a variable resistive value as a function of the temperature, the resistive value of the resistor being greater than the resistive value of the electrical contacts formed each by at least one metallic layer of a total thickness of between 50 and 150 nanometers.

The electrical heating resistor forms at least partly the bottom or is arranged under the bottom of at least one culture well containing said at least one cell culture.

A plurality of culture wells intended to contain a plurality of cell cultures is arranged on a support comprising a plurality of electrical heating resistors for cell cultures, the electrical heating resistors being arranged to form at least partly the bottom of the culture wells or being arranged under the bottom of the culture wells.

The prescribed setpoint temperature is constant and equal to a determined temperature for growth of living cells in the cell culture.

The second parameter representative of the time development of the cell culture is the area covered by the cells of the cell culture on the receiving surface or the percentage of area covered by the cells of the cell culture relative to the area of the receiving surface.

A second subject matter of the invention is a process for monitoring the development of at least one cell culture by means of the device such as described hereinabove, in which a cell culture is arranged on a receiving surface for receiving the cell culture, the receiving surface being in contact with electrical impedance arranged to have an impedance time value influenced by the presence of cells in the cell culture, characterised in that the impedance comprises an electrical heating resistor, the cell culture is heated by the electrical heating resistor in contact with the receiving surface, the resistor being connected to an electrical circuit for supplying heating energy to the resistor, the resistor being variable as a function of the temperature and located in a heat control loop forming the electric heating circuit to maintain the cell culture at a prescribed setpoint temperature, at least one first parameter representative of the quantity of heat energy consumed by the electrical circuit is measured by a measuring element of the heat control loop, this measuring element serving also as measuring element for measuring the development of the cell culture, the measuring element being distinct from the resistor, at least one second parameter representative of the time development of the cell culture is calculated by at least one calculator from the first parameter representative of the quantity of heat energy consumed by the electrical circuit.

Figure 4:
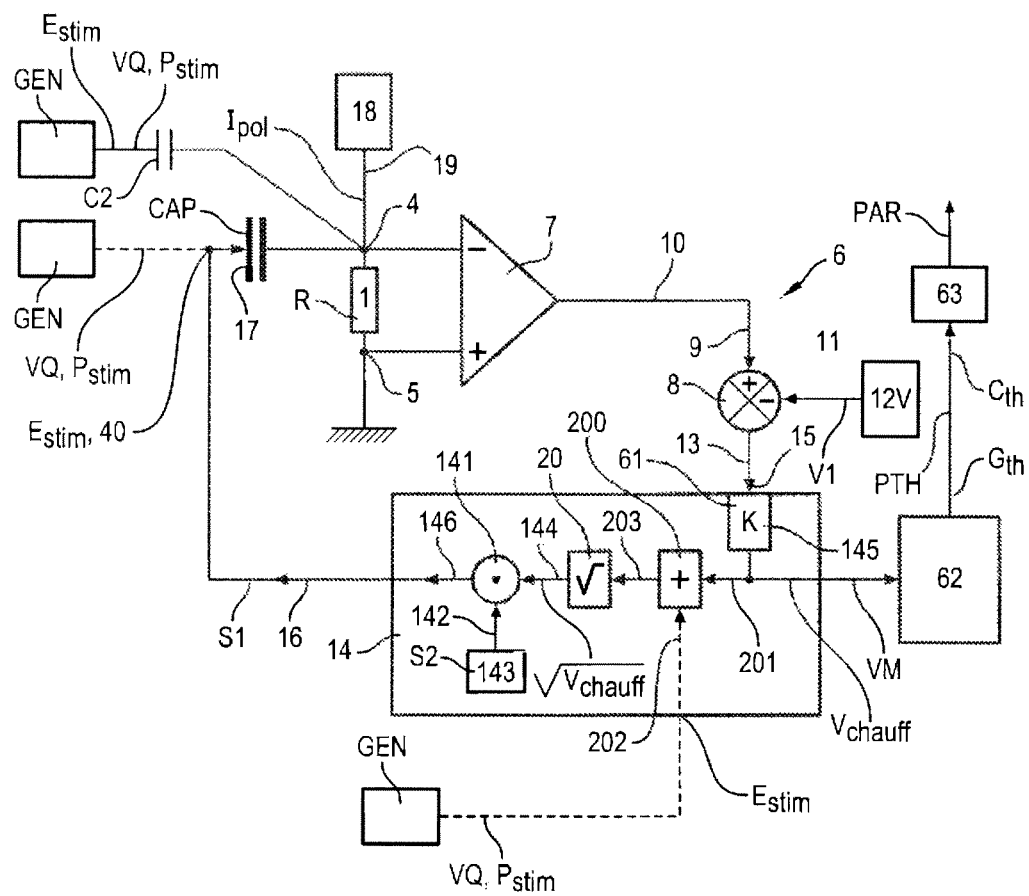
Figure 5:
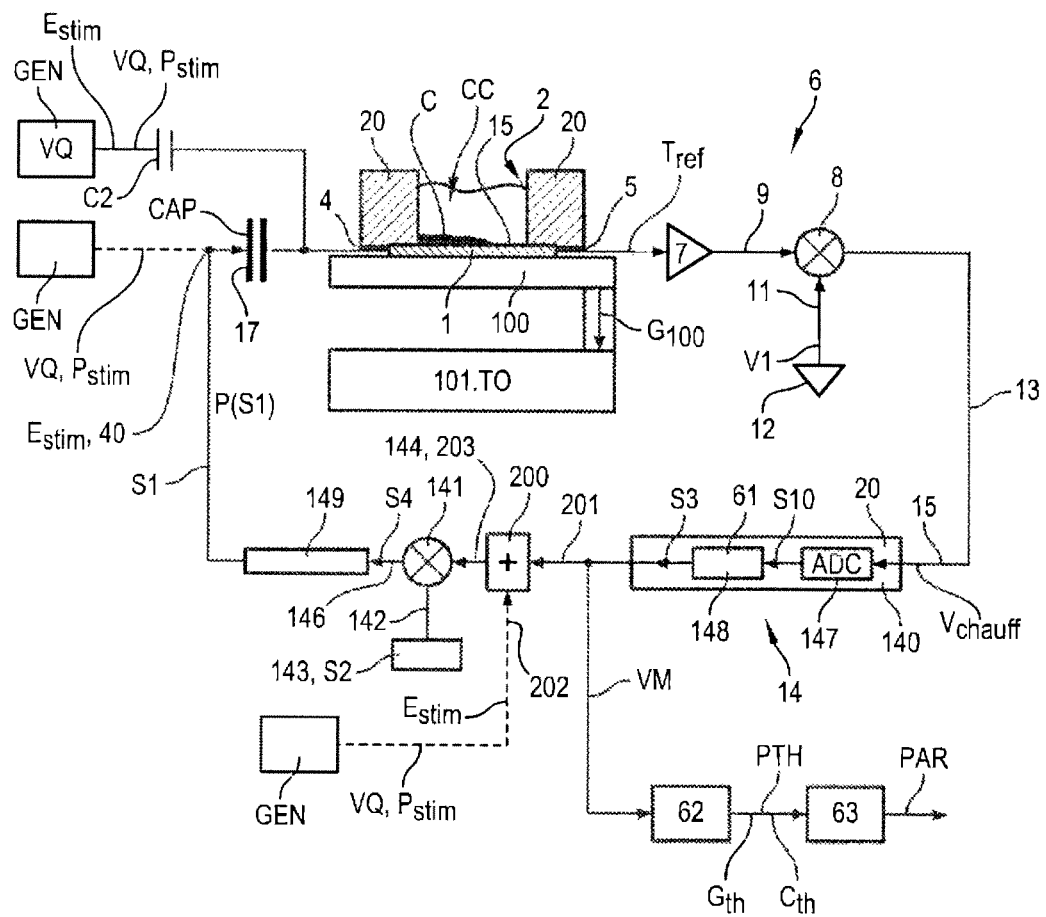
Figure 6:
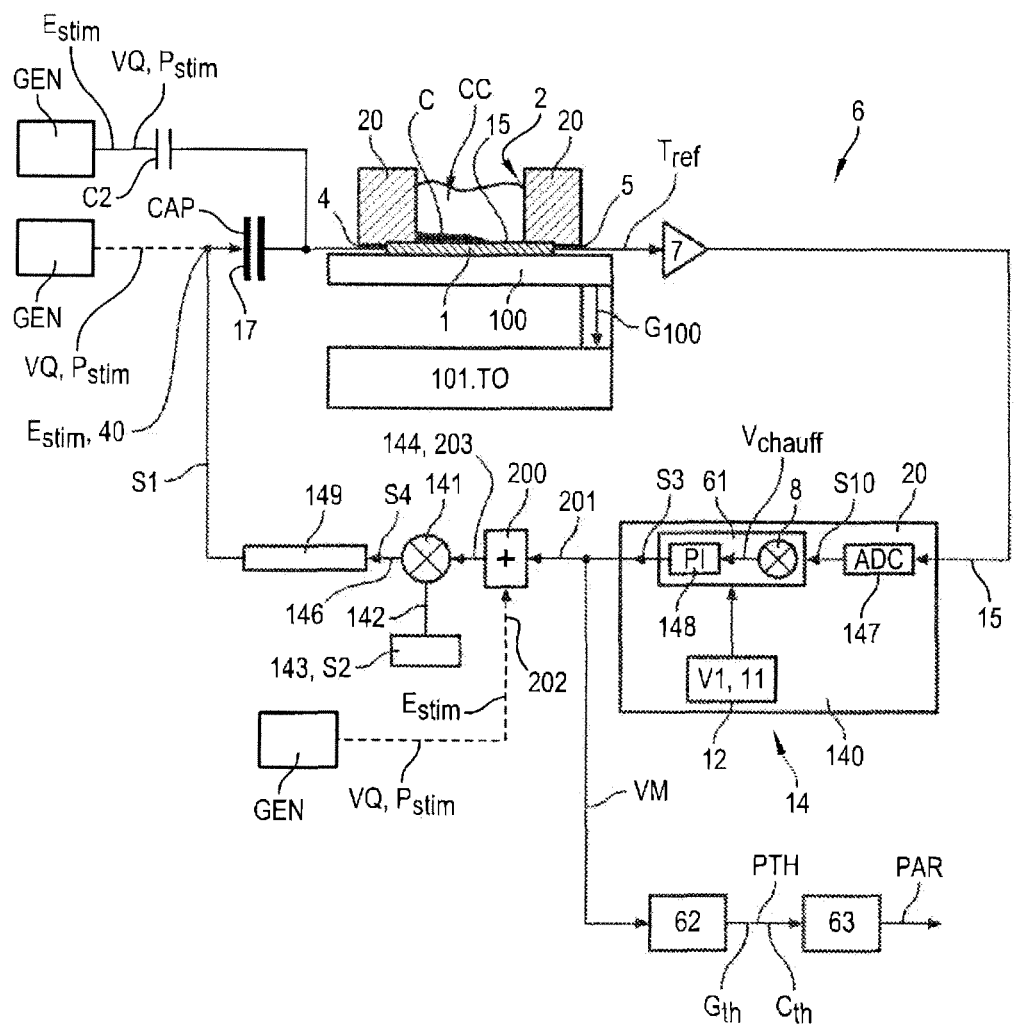
Figure 7:
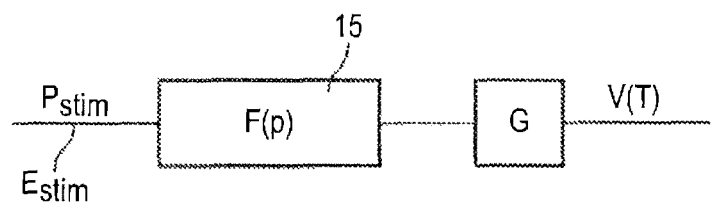
Figure 8:
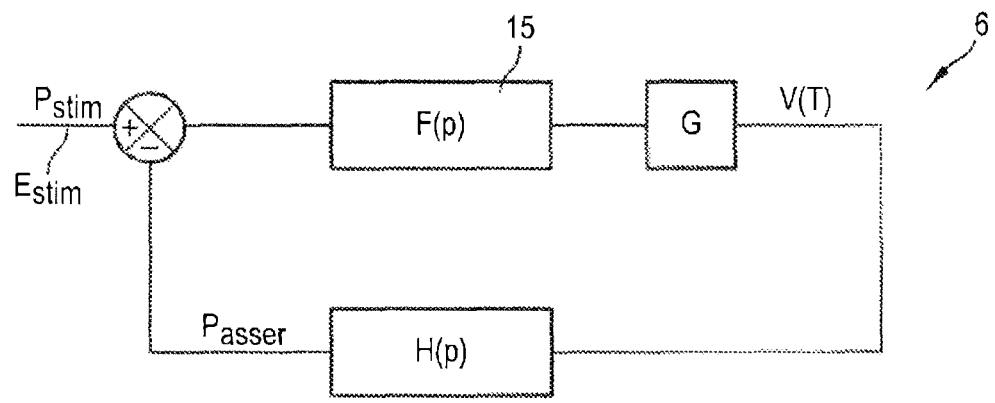

The invention will be more clearly understood from the following description, given purely by way of non-limiting example in reference to the attached diagrams, in which:

FIG. 1 is a schematic view in vertical section of a receiving surface of cell culture, linked to a heating resistor, according to an embodiment, FIG. 2 is an electrical diagram of the control device according to the invention, FIG. 3 is an electrical diagram of the control device according to the invention, according to a first embodiment, FIG. 4 is an electrical diagram of the control device according to the invention, according to a second embodiment, FIG. 5 is an electrical diagram of the control device according to the invention, according to a third embodiment, FIG. 6 is an electrical diagram of the control device according to the invention, according to a variant of the third embodiment, FIG. 7 is an equivalent diagram of the resistor of the device in open loop, FIG. 8 is an equivalent diagram of the resistor of the device in closed loop.

In the figures, a receiving well 2 of a cell culture CC is provided above an electrical heating resistor 1 for heating the culture CC. The well 2 is delimited laterally by walls 20, for example vertical walls. The resistor 1 is on an insulating support 100, for example by being photo-etched on the upper surface 101 of the insulating support 100 to form a printed circuit. The resistor 1 comprises a first end 110 connected to a first electrical contact 4 and a second end 120 connected to a second electrical contact 5. Between the first end 110 and the second end 120, the electrical resistor 1 has a resistive value R in ohms which is variable as a function of the temperature. The electrical resistor 1 is at least partly under the cell culture CC.

The cell culture CC contains living cells C cultivated in a nutritive liquid medium, provided for the growth of the cells C. This culture medium usually comprises around 90% water, nutrients and oligo-elements which have to be consumed to make the cells grow and multiply. The majority of the cells C settle by sedimentation at the bottom of the well 2. Of course, any substance the impact of which on the cells is to be detected can have been added to the cell culture CC.

The device forms a sensor of cells C in the culture CC. In the embodiment illustrated in FIG. 1, the upper surface 15 of the resistor 1 forms at least partly the receiving surface of the cell culture C, that is, it is in direct contact with this liquid cell culture CC.

In the embodiment illustrated in FIG. 1, the entire bottom of the well 2 is formed by the upper surface 15 of the resistor 1.

A standard culture well 2 covers for example a base area of 1 $cm^2$ on the resistor 1 for a height of around 1 cm, and represents a volume of around 1 $cm^3$.

The electrical contacts 4 and 5 each form a conductive area having a resistive value less than the resistive value R of the resistor 1. The resistor 1 is made of metal for example, and can be made of gold or platinum, with a total thickness of between 5 and 20 nanometers, for example for heating a culture surface of 1 $cm^2$. The electrical contacts and 5 are formed for example by one or more metallic layers of a total thickness of between 50 and 150 nanometers. For example, the electrical contacts 4 and 5 each have a part respectively 41, 51 covering the ends 110 and 120 of the resistor 1.

The resistor 1 is connected by its electrical contacts 4 and 5 to a heat control loop 6 forming an electric circuit for heating of the resistor 1. This heat control loop 6 is for example of the type described in document WO 2009/034066 A1. The heat control loop 6 is provided to keep the temperature of the resistor 1 equal to a setpoint temperature Tref and for heating the resistor 1.

The prescribed temperature setting Tref is the temperature necessary for the life of the cells C in the culture CC and is constant for example. This temperature setting Tref is for example 37° C. This temperature Tref is that provided to allow normal growth of the cells C in the culture CC in the presence of the culture medium contained in the well 2. The loop 6 therefore keeps the temperature of the resistor 1, of the surface 15 and the culture CC at a constant temperature. The loop 6 comprises a corrector 14 of application of heating power to the resistor 1 to keep the temperature of the resistor 1 at the temperature setting Tref. For example, as will be described hereinbelow, the corrector 14 is provided to generate a frequential component S1 of the heating power, which is applied to a first coupling means 17 provided between the resistor 1 and the corrector 14 for applying to the resistor 1 a signal without direct current component, second coupling means 19, distinct from the first coupling means 19, provided between the resistor 1 and direct current polarisation means 18 to keep the electrical resistor 1 at a direct current prescribed operating point.

Of course, the preset temperature setting Tref could be different to the temperature of life or growth of the cells C in the culture CC, for example for the purpose of testing cells C at this different temperature.

The heat control loop 6 comprises a measuring element 61 for measuring of the quantity of heat energy consumed to keep the resistor 1 at the preset temperature setting Tref. This measuring element 61 is therefore distinct from the resistor 1 serving as heating of the cell culture CC. The element 61 supplies a measuring signal VM of the quantity of heat energy consumed. This signal VM is a first parameter representative of the quantity of heat energy consumed by the electrical circuit to maintain the prescribed setpoint temperature Tref.

A calculator 62 calculates from the signal VM measuring the quantity of heat energy consumed, provided by the measuring element 61, a second parameter PAR representative of the time development of the cell culture CC.

The thermal parameters PTH of the cell culture surface 15 are extracted without modifying its temperature. To do this, the calculator 62 first calculates the thermal parameters of the resistor 1 heating the cell culture CC, these thermal parameters comprising for example the thermal capacity $C_{th}$ and/or the thermal conductance $G_{th}$ viewed by the resistor 1 over time when it is subjected to the cell culture CC.

In fact, the quantity of heat which the heating resistor 1 should supply to the cell culture CC will not be the same according to whether there are more or fewer cells C in the well 2 and especially at the bottom of the well 2.

In fact, the inventor noticed that the more living cells C there were at the bottom of the well 2, the less the culture CC had to be heated and the less the resistor 1 had to contribute heat.

Measuring the variation in thermal properties of the surface 15 during evolution of the cell population C is used in this way. As they grow, the cells C cover the surface 15 or the bottom of the well 2 and the heat transfers between the surface 15 and the culture medium CC are different as per the presence or not of cells between the latter. Measuring the thermal parameters, conductance and capacity at the surface 15 gives an indication of the evolution of the cell population C.

So in the absence of cells C, the interface between the surface 15 and the culture medium CC is the epicentre of a heat convection phenomenon $Q_2$ going from the resistor 1 (heating surface) to the fluid CC (culture medium), as is illustrated in FIG. 1. In the presence of cells C, the exchange is made by thermal conduction between the surface 15 of the resistor 1 and the cells C, then by convection between the cells C and the culture medium CC, as is illustrated overall by the heat flow $Q_1$ in FIG. 1. These thermal phenomena of different types involve different thermal characteristics for the environment of the culture surface according to the presence or the absence of cells. Accordingly, in determining the evolution of thermal parameters of the culture surface over time, the evolution of the cell population C is tracked at the culture surface. In FIG. 1, the heat flow $Q_3$ represents the heat provided by the heating resistor 1 to the support 100 having determined thermal conductivity $G_{100}$. Hereinbelow the surface 15 of the resistor 1 turned towards the cell culture CC is called cell culture surface 15.

An example of calculation by the calculator 62 of a third thermal parameter Pth, specifically the thermal capacity $C_{th}$ and/or the thermal conductance $G_{th}$ is described hereinbelow.

Analysis of the response of the global system (closed loop) to an external stimulation of power $P_{stim}$ on an input $E_{stim}$ of the electrical circuit will give access to searched magnitudes which are conductance and thermal capacity, as specified hereinbelow. Detection of cells C by the device is thermal. This external stimulation $P_{stim}$ is contributed by an external generator GEN connected electrically to the loop 6. The input $E_{stim}$ is therefore connected to the generator GEN.

The open thermal system constituted by the cell culture surface 15 will be considered. The thermal parameters, conductance $G_{th}$ and capacity $C_{th}$ of the cell culture surface 15 evolve over time as a function of the growth of the cells.

Let F(p) be the representation of the thermal system in FIG. 7:

$$F(p) = \frac{A}{G_{th}(1 + \tau_{th}p)}$$

With $$\tau_{th} = \frac{C_{th}}{G_{th}}$$

G represents the gain of the conditioning electronics and the transfer of temperature measuring.

With a conventional corrector H(p) of proportional-integral type in the loop 6 in FIG. 8:

$$H(p) = \frac{1 + Kp}{p}$$

the global loop system, that is, the loop 6 becomes:

$$P_{asser}(p) = \frac{A(1 + Kp)}{1 + \frac{G + AK}{A}p + \frac{C_{th}}{A}p^2} P_{stim}(p)$$

with F(p) receiving at input the difference ($P_{stim}$ (p)–$P_{asser}$ (p)) and H(p) in series with F(p) and G.

Analysis of transitional systems (overshooting, oscillation, damping) in case of stimulation of impulse type or of the frequential response in case of stimulation of frequential type will be traced to the parameters $C_{th}$ and $G_{th}$ and therefore to covering of the culture surface 15 by the cells.

An adaptive corrective system can be considered for keeping servo performances constant.

Given the slow rate of phenomena to be tracked, growth of cells, multiple acquisitions could be made and averaged to improve resolution.

Due to its simple concept, this method of tracking cellular growth can easily be parallelised to be combined with devices of plate type with several wells.

The external stimulation $P_{stim}$ is for example a variation of heat VQ. The external stimulation signal $P_{stim}$ in the form of an electric signal $P_{stim}$ is applied to a determined point of the loop 6.

As external stimulation $P_{stim}$, the variation of heat VQ is applied to the terminal 4 for example in the form of an electric signal $P_{stim}$ by means of an electric capacitor C2, whereof the terminal other than that connected to the terminal 4 forms the input $E_{stim}$. The coupling means 17 or capacity 17 described hereinbelow can also be used by adding the external stimulation signal $P_{stim}$ to the servo signal S1 electrically, for example by applying the external stimulation signal $P_{stim}$ directly to the capacity 17 at its terminal 40 other than that connected to the terminal 4, this terminal 40 of capacity 17 forming the input $E_{stim}$.

In a preferred embodiment, the external stimulation signal $P_{stim}$ is added to the signal VM to provide the resulting sum at the input 144 which will be described hereinbelow and which provides the servo signal S1 of the resistor 1 in the loop 6. In this case the corrector 14 therefore comprises the input $E_{stim}$, to which the external stimulation signal $P_{stim}$ is applied, and an adding module 200 of this input $E_{stim}$, which will be described hereinbelow.

The signal $P_{stim}$ applied to the input $E_{stim}$ is for example of the same type as the signal S1 which will be described hereinbelow. The signal $P_{stim}$ applied to the input $E_{stim}$ is for example an alternative electric signal having a frequential component of zero mean, which can be high-frequency, for example in a frequency band where the lower limit is at least 20 kHz. The electric signal $P_{stim}$ applied to the input $E_{stim}$ can be sinusoidal. The electric signal applied to the input $E_{stim}$ can also be impulse. The external stimulation $P_{stim}$, VQ on the input $E_{stim}$ serves as heating of the resistor 1. Hereinbelow this electric signal $P_{stim}$, VQ is added to the signal S1 at the terminals of the resistor 1. The predetermined signal VQ, $P_{stim}$ of external thermal stimulation is therefore applied to the loop 6.

A calculator 63 calculates the second parameter PAR representative of the time development of the cell culture from the thermal parameter or thermal parameters Pth, such as for example the thermal capacity $C_{th}$ and the thermal conductance $G_{th}$, said parameter PAR being for example the area covered by the cells C in the bottom of the well or the percentage of coverage of cells relative to the total area of the bottom of the well 2.

For example, signals utilised by the calculators, VM for example, are converted from analog to digital by an analog-digital converter. The calculators 62 and 63 can do one only and be formed for example by a computer. The calculators comprise automatic calculation means for this purpose.

Different embodiments of the loop 6 are described hereinbelow. The principle of electrical substitution by capacitive coupling is used.

In a first embodiment illustrated in FIGS. 2 and 3, the loop 6 comprises: a device 7 for amplification of the voltage on terminals 4, 5 of the resistor 1, a subtractor element 8 comprising a first input 9 connected to the voltage output 10 of the amplification device 7 and a second input 11 connected to a module 12 imposing voltage VI of constant prescribed setpoint to form on an output 13 of the subtractor 8 the difference Vchauff or error signal between the two inputs 9, 11. The output 13 of the subtractor 8 is connected to the input 15 of a corrector module 14 applying via its output 16 an alternative signal S1 which is a function of the signal present at its input 15. The output 16 is connected to the resistor 1 by first coupling means 17.

In FIG. 3, a module 18, distinct from the heat control loop 6, is provided to impose prescribed polarisation Ipol of the operating point of the resistor 1 in direct current by means of second coupling means 19, whereas the first coupling means 17 apply to the resistor 1 a frequential component S1 of zero mean. For example, in FIG. 3, the coupling means 17, 19 are connected to the same node formed by the first terminal 4 of the resistor 1, whereof the second terminal 5 is connected to the earth.

The frequential signal S1 serves as heating for the resistor 1.

The counter-reaction of heat by the heating signal S1 controls the temperature of the resistor 1 at the temperature Tref without modifying its operating point linked to the polarisation current Ipol passing through it.

In an embodiment, the resistive element or the resistive elements for heating of the culture CC in the loop 6 comprise only the resistor 1.

In the embodiment illustrated in the figures, the first coupling means 17 is capacitive and comprise one or more capacitors forming a capacity CAP of determined value. The second coupling means 19 are formed by simple electrical conductors.

The heating signal S1 is for example a high-frequency signal in a frequency band greater than 20 kHz.

In an embodiment, the corrector 14 forms a first heating signal S1, which is sinusoidal and for example proportional to the signal on the input 15. The heating signal S1 is for example formed by amplitude modulation of the difference signal Vchauff by a second sinusoidal signal S2 having said frequency. For this purpose the corrector 14 comprises for example a multiplier 141 comprising a first input 142 connected to a module 143 for providing the second sinusoidal signal sin(ω·t), a second input 144 connected to the input 15, for example by means of a module 145 bringing a constant prescribed multiplicative factor K and optionally by means of the optional adding module 200 which will be described hereinbelow, and an output 146 connected to the output 16. The elements 141, 143 form means of modulation of the intermediate signal on the input 144 by the sinusoidal signal S2 to form the alternating signal S1.

It is supposed hereinbelow that the input 144 is connected directly to the module 145 without the adding module 200. There is for example in this case:

$$S1 = Vchauff \cdot \sin(\omega \cdot t)$$

with
Vchauff the signal present on the input 144,
t the time,
ω a prescribed pulsation.
The current passing through the measuring resistor R is:

$$i(t) = Ipol + (Vchauff/R) \cdot \sin(\omega t)$$

The average value of i(t) is equal to Ipol.
The power p(t) in the resistor 1 is:

$$p(t) = R \cdot \{Ipol2 + 2 \cdot Ipol \cdot (Vchauff/R) \cdot \sin(\omega \cdot t) + ((Vchauff/R) \cdot \sin(\omega t))2\}$$

and has an average value $$\overline{p}(t) = R \cdot I_{pol}^2 + \frac{1}{2} \frac{V_{chauff}^2}{R}$$

The power dissipated in the resistor 1, and consequently its temperature, can therefore be changed without changing its operating point, given that the average current passing through the measuring resistor remains constant to Ipol.

In FIG. 2, the measuring element 61 is for example formed by the corrector 14. More precisely, in FIG. 3 this measuring element 61 of the quantity of heat energy is formed by the element 145 supplying the signal $V_{chauff}$. This signal $V_{chauff}$ is representative of the quantity of power provided by the loop 6 to the resistor 1. This signal $V_{chauff}$ is sent from the corrector 14 to a calculator 62, which calculates from this signal of energy quantity the parameter PAR representative of the time development of the cell culture CC.

In the case where the adding module 200 is provided in FIG. 3, this adding module 200 comprises a first input 201 connected to the signal $V_{chauff}$ and to the module 145, a second input 202 connected to the input $E_{stim}$ of external stimulation signal $P_{stim}$, and an output 203 connected to the input 144. The adding module 200 provides on its output 203 and therefore on the input 144 the sum of the signal $V_{chauff}$ and of the external stimulation signal $P_{stim}$.

Of course, several heating resistors 1 can be provided for heating several culture wells 2, the resistors 1 being connected in the same electrical circuit or in different electrical circuits. For example, several wells 2 each with their associated loop 6 can be provided on the same support 100. Several resistors 1 can be provided in parallel in the same electrical circuit.

In other embodiments, the heating resistor or the heating resistors 1 could be insulated electrically from the culture medium CC. Given the orders of magnitude of the necessary resistors, of the order of around a hundred Ohm, the thickness of the metallic layers employed to make them will be lower (5 to 20 nanometers) than that used conventionally to make electrodes (>150 nanometers). This metallic layer is for example made of gold or platinum. This makes the manufacturing process less expensive, both because fewer metals are utilised, and because this small thickness even ensures semi-transparency of the support, enabling observation by transmission microscope during cultures. Configurations of resistive surface elements 1 in the form of grilles can also be considered.

In other embodiments not illustrated here, a very fine layer of material is provided between the upper surface 15 of the resistor 1 and the cell culture CC, this layer therefore forming the bottom of the well 2 and therefore the receiving surface of the cell culture. This layer is for example provided to prevent direct contact of the cell culture CC with the resistor 1, in the case where the material of the resistor is likely to interact with the cells or the cell culture.

In an embodiment, the device is in the form of an electronic casing having a computer interface linked to disposable culture slides covered in several culture wells, or not covered, and exhibiting a surface or surfaces insulated electrically from cells for utilising the slaving of heat by electrical substitution and capacitive coupling for extraction of electrical parameters. The casing implements slaving of heat by electrical substitution and capacitive coupling, whereas the disposable culture slides will constitute a purely passive device easily manufactured at low cost.

In a second embodiment illustrated in FIG. 4 and in accordance with the first embodiment of FIGS. 2 and 3, there are also means 20 for linearising the power of the signal S1 as a function of the difference signal $V_{chauff}$ or of the temperature signal measured by the element 1. In FIG. 4, these linearisation means 20 for example have the form of a square root formation module arranged upstream of the multiplier 141 of amplitude modulation and downstream of the input 15, for example between the module 145 and the multiplier 141 (or as a variant between the module 145 and the input 15). The module 20 forms on the input 144 a signal proportional to $\sqrt{V_{chauff}}$ in the case where the input 144 is connected directly to the module 145. The power P(S1) of the signal S1 applied by the means 17 to the element 2 is proportional to the difference signal $V_{chauff}$. In FIG. 3, the measuring element 61 of the quantity of heat energy is formed by the element 145 supplying the signal $V_{chauff}$, which is representative of the quantity of power provided by the loop 6 to the resistor 1. In the case where the adding module 200 is provided, this module 200 such as described hereinabove is for example provided upstream of the module 20 as illustrated to provide on the input 144 a signal proportional to the sum $\sqrt{(V_{chauff} + P_{stim})}$, the input of the module 20 being connected at the output 203 of this adding module 200 and the second input 202 of this adding module 200 being connected to the input $E_{stim}$ of external stimulation signal $P_{stim}$. Of course, the adding module 200 could also be provided downstream of the module 20, with the output 203 connected directly to the input 144 and the first input 201 connected to the output of the module 20.

In the third embodiment illustrated in FIG. 5, the linearisation means 20 of the power of the signal S1 as a function of the difference signal $V_{chauff}$ have another form. The difference signal $V_{chauff}$ is digitised in the digital corrector 14. The difference signal can also be formed in the controller by digitising of the signal 9 and calculation of the difference with a value stored in the controller. This corrector 14 is executed by a microcontroller 140, a microprocessor, a microcomputer, or others. For this purpose, the difference signal $V_{chauff}$ is sent in the corrector 14 to an analog-digital converter 147 (ADC) supplying a digital signal S10 from the analog difference signal $V_{chauff}$ present on the input 15 of the corrector 14. This digital signal S10 is modulated in pulse width (PWM for "pulse width modulation") by a pulse width modulation module 148, comprising for example a proportional and integral corrector PI for applying proportional and integral correction to the signal S10, to form a intermediate third signal S3, known as heating retroaction signal. The cyclic ratio β of the third intermediate signal S3 in pulse width modulation is equal, expressed in %, to β=100·tON/T where
tON is the time during which the signal S3 is at a first level, for example the top level 1,
T is the prescribed and constant period of the signal S3,
tOFF=T−tON is the time during which the signal S3 is at a second level different to the first level, this second level being for example the low level. The average value of the intermediate third signal S3 in pulse width modulation is equal to the value of the signal at output of the controller.

The corrector 14 provides the intermediate third signal 53 on the input 144. The input 144 is connected for example directly hereinbelow to the multiplier 141 to carry out amplitude modulation of the intermediate third signal S3 by the second sinusoidal carrier signal S2 of the module 143, to provide on the output 146 a fourth sinusoidal signal S4 for one only of the first and second level of S3, for example for the first level corresponding to tON and a constant signal, zero for example, for the other level of S3, for example for the second level corresponding to tOFF. The fourth signal S4 is then sent to the coupling means 17 to form the frequential signal S1 for example by means of a band pass filter 149 around the frequency of the carrier S2.

The value calculated by the proportional and integral controller as a function of the signal S10 is equal to the average value of the signal S3, that is, equal to β·Vmax· with Vmax the maximal voltage at the output of the digital component for a cyclic ratio β of 100%.

$$S2 = Kampl \cdot \sin(\omega \cdot t)$$

$$S4 = Kmult \cdot S3 \cdot S2 = Kmult \cdot Kampl \cdot \sin(\omega \cdot t) \cdot S3$$

with Kampl a constant and Kmult a constant linked to the multiplier.
The RMS value of the signal S4 is $$V_{RMS}(S4) = \sqrt{\frac{1}{T}\int_0^T (K_{mult} \cdot S3 \cdot S2)^2 \, dt}$$

that is $$V_{RMS}(S4) = \sqrt{\frac{1}{T}\int_0^{\beta T} (K_{mult}^2 \cdot V_{max}^2 \cdot S2)^2 \, dt}$$

$$V_{RMS}(S4) = \sqrt{\frac{\beta}{2} K_{mult}^2 \cdot V_{max}^2 \cdot K_{ampl}^2}$$

$$V_{RMS}(S4) \propto \sqrt{\beta}$$

$$P(S1) = \frac{V_{RMS}^2(S4)}{R_{mes}} \propto \beta \propto S3 \propto V_{chauff}$$

where P(S1) is the power of the signal S1 and the sign c signifies proportionality.

The power of counter-reaction applied to the resistor 1 is therefore directly proportional to the value calculated at the output of the controller 148. The system is then entirely linear. There is no need to hypothesis for linearisation and calculation of correctors.

Pulse width modulation enables linearisation of the power of the signal S1 as a function of the difference signal $V_{chauff}$. The linearisation could of course be used as in analog by the use of a digital square root function, but using pulse width modulation PWM directly allows linearisation without additional function or other calculation.

In the case where the adding module 200 is provided, this module 200 such as described hereinabove is for example provided upstream of the module 141 and downstream of the module 148 as illustrated in FIG. 5, the input 144 being connected to the output 203 of this adding module 200, the input 201 being connected to the output of the module 148 supplying the signal S3 and the input 202 being connected to the input $E_{stim}$ of external stimulation signal $P_{stim}$. The adding module 200 provides the sum of the signal S3 and of the external stimulation signal $P_{stim}$ at its output 203 and therefore at the input 144.

In FIG. 5, the measuring element 61 for measuring the quantity of heat energy is formed by the element 148 supplying on its output the signal S3 which is representative of the quantity of power provided by the loop 6 to the resistor 1.

Of course, in the embodiments described hereinabove, the amplitude modulation can be done using a multiplier 141 or a simple interrupter, for example with transistor(s).

FIG. 6 is a variant of FIG. 5, where the difference signal $V_{chauff}$ is digital and is formed after conversion of the analog temperature signal present on the output 9 into a digital signal in the analog-digital converter 147, the output 9 being connected directly to the input 15. The elements 8, 11 and 15 are digitised to form the digital difference $V_{chauff}$ between the digitised output 9 at the output S10 of the converter 147 and the constant digital signal VI provided by a digital module 12. The digital difference signal $V_{chauff}$ is sent to the module 148. The constant digital value V1 is a preregistered setpoint value in a memory 12 of the microcontroller or others.

In FIG. 6, the measuring element 61 for measuring the quantity of heat energy is formed by the element 148 supplying on its output the signal S3 which is representative of the quantity of power provided by the loop 6 to the resistor 1.

The multiplier 141 can be connected either directly to the output of the module 148 to receive the signal S3 on the input 144, or be connected as illustrated to the output of the module 148 by means of the adding module 200 such as described hereinabove in reference in FIG. 5, to have on the input 144 the sum of the signal S3 and of the signal $P_{stim}$, the input 202 of the adding module 200 being connected to the input $E_{stim}$ of external stimulation signal $P_{stim}$.

Because of the invention, the detection of cells is integrated on the culture support. This avoids the stress imposed on cell cultures, due to handling cultures (output incubator). Constraints on the acquisition of data are diminished by dispensing with the use of a microscope in a confined environment. There is no need for optical observation of cells, or for dyeing or fluorescence. Parallel monitoring in real time is made possible.

Other advantages are also the simplicity of the sensor 1, the ease of integration, the absence of electrical interaction, the low cost and the fact that control is non-invasive.

LIST OF DOCUMENTS CITED

[1] "Monitoring cell cycle by impedance spectroscopy: experimental and theoretical aspects" Eugen Gheorghiu, Koji Asami, Bioelectrochemistry and Bioenegetics 45 (1998) 139-143;

[2] "Analysis of the 3-omega method for thermal conductivity measurement" Hainan Wang, Mihir Sen, International Journal of Heat and Mass Transfer 52 (2009) 2102-2109;

[3] "Determination of thermal conductivity in liquids by monitoring transient phenomenon" Juraj Bozicevic, Alojz Caharija, Nena Bolf, Denis S. Vedrina, Procedings, XVII IMEKO World Congress, Jun. 22-27, 2003, Dubrovnik, Croatia;

[4] "A micromachined AC thermal sensor for monitoring the liquid-gas interface in a microchannel", Sun Rock Choi, Jonggan Hong, Dongsik Kim, Sensors and Actuators A 150 (2009) 40-45;

[5] "Fibroplast Cells: A Sensing Bioelement for Glucose Detection by Impedance Spectroscopy", Chaker Tlili, Karine Reybier, Alain Geloen, Laurence Ponsonnet, Claude Martelet, Hafedh Ben Ouada, Michel Lagarde and Nicole Jaffrezzic-Renault, Anal. Chem. 2003, 75, 3340-3344.

The invention claimed is:

1. A device for monitoring the development of at least one cell culture, comprising a receiving surface for receiving the cell culture,
the receiving surface being in contact with at least one electrical heating resistor for the heating of the cell culture, the at least one electrical heating resistor being variable as a function of the temperature and being part of a heat control loop,
wherein the heat control loop further comprises a corrector for supplying a quantity of electrical energy to the at least one electrical heating resistor to maintain the cell culture at a prescribed setpoint temperature and at least one measuring element for measuring at least one first parameter representative of the quantity of electrical energy supplied by the corrector to the at least one electrical heating resistor, this measuring element also serving as measuring element for measuring the development of the cell culture, the measuring element being distinct from the at least one electrical heating resistor, the device further comprising at least one calculator for calculating at least one second parameter representative of the time development of the cell culture from the first parameter representative of the quantity of electrical energy supplied by the corrector to the at least one electrical heating resistor,
a generator of a predetermined signal of external thermal stimulation connected to a determined point of the heat control loop, the calculator being provided for calculating at least one third parameter being at least one thermal parameter from the first parameter representative of the quantity of electrical energy supplied by the corrector to the at least one electrical heating resistor, the third parameter being calculated by the calculator from the response of the at least one electrical heating resistor to the signal of external thermal stimulation, said second parameter representative of the time development of the cell culture being calculated by the calculator from said third parameter.

2. The device as claimed in claim 1, wherein the third parameter comprises the thermal capacity of the at least one electrical heating resistor when it is in the presence of the cell culture and/or the thermal conductance of the at least one electrical heating resistor when it is in the presence of the cell culture.

3. The device as claimed in claim 1, wherein the signal of external thermal stimulation is applied to one of the terminals of the at least one electrical heating resistor by means of at least one electric capacitor.

4. The device as claimed in claim 1, wherein the signal of external thermal stimulation is applied to an adding module comprising a first input on which the measuring signal is located, a second input connected to the determined point of the heat control loop, to which the signal of external stimulation is applied, and an output supplying a servo signal of the at least one electrical heating resistor equal to the sum of the signals present on the first input and on the second input.

5. The device as claimed in claim 1, wherein the signal of external thermal stimulation is in the form of an electric signal having a frequential component of zero average.

6. The device as claimed in claim 1, wherein the signal of external thermal stimulation is in the form of an electric impulse signal.

7. The device as claimed in claim 1, wherein the at least one electrical heating resistor forms at least partly the receiving surface of the cell culture.

8. The device as claimed in claim 1, wherein the receiving surface of the cell culture is provided on electrically insulating material interposed between the at least one electrical heating resistor and the cell culture.

9. The device as claimed in claim 8, wherein the electrically insulating material interposed between the at least one electrical heating resistor and the cell culture is fixed removably relative to the at least one electrical heating resistor.

10. The device as claimed in claim 1, wherein the at least one electrical heating resistor is metallic with a thickness of between 5 and 20 nanometers.

11. The device as claimed in claim 10, wherein the at least one electrical heating resistor comprises a first end connected to a first electrical contact and a second end connected to a second electrical contact, the at least one electrical heating resistor having between the first end and the second end a resistive value variable as a function of the temperature, the resistive value of the at least one electrical heating resistor being greater than the resistive value of the electrical contacts formed each by at least one metallic layer of a thickness of between 50 and 150 nanometers.

12. The device as claimed in claim 1, wherein the at least one electrical heating resistor forms at least partly the bottom or is arranged under the bottom of at least one culture well containing said at least one cell culture.

13. The device as claimed in claim 12, wherein a plurality of culture wells intended to contain a plurality of cell cultures is arranged on a support comprising a plurality of electrical heating resistors of cell cultures, the electrical heating resistors being arranged to form at least partly the bottom of the culture wells or being arranged under the bottom of the culture wells.

14. The device as claimed in claim 1, wherein the prescribed setpoint temperature is constant and equal to a determined temperature for growth of living cells in the cell culture.

15. The device as claimed in claim 1, wherein the second parameter representative of the time development of the cell culture is the area covered by the cells of the cell culture on the receiving surface or the percentage of area covered by the cells of the cell culture relative to the area of the receiving surface.

16. A process using the device of claim 1, comprising:
heating a cell culture by the electrical heating resistor,
measuring the at least one first parameter
generating a predetermined signal of external thermal stimulation by a generator connected to a determined point of the heat control loop,
calculating at least one second parameter representative of the time development of the cell culture by at least one calculator from the first parameter representative of the quantity of electrical energy supplied by the corrector to the electrical heating resistor, the calculator being provided for calculating from the first parameter at least one third parameter being at least one thermal parameter, calculating the third parameter by the calculator from a response of the at least one electrical heating resistor to a signal of external thermal stimulation, said second parameter representative of the time development of the cell culture being calculated by the calculator from said third parameter.

* * * * *